United States Patent [19]
Harrison et al.

[11] Patent Number: 5,538,005
[45] Date of Patent: Jul. 23, 1996

[54] B'METHOD FOR MONITORING FETAL CHARACTERISTICS BY RADIOTELEMETRIC TRANSMISSION

[75] Inventors: Michael R. Harrison, San Francisco; Russell W. Jennings, Pacifica, both of Calif.

[73] Assignee: The Regents of the University of California, Alameda, Calif.

[21] Appl. No.: 400,579

[22] Filed: Mar. 8, 1995

Related U.S. Application Data

[62] Division of Ser. No. 81,139, Jun. 25, 1993, Pat. No. 5,431,171.

[51] Int. Cl.$^6$ .................................................. A61B 5/0444
[52] U.S. Cl. ............................................................ 128/698
[58] Field of Search ..................... 128/698, 898, 128/903

[56] References Cited

U.S. PATENT DOCUMENTS 5,425,362   6/1995   Siker et al. .............................. 128/635

OTHER PUBLICATIONS

Harrison et al., 'Radiotelemetric fetal monitoring during and after open fetal operation', Surgical and Gynecological Obstetrics Jan. 1993, pp. 59–64.

Harrison et al., 'New Techniques in Fetal Surgery', Journal of Pediatric Surgery, Oct. 1992, pp. 1329–33.

*Primary Examiner*—William E. Kamm
*Assistant Examiner*—Scott M. Getzow
*Attorney, Agent, or Firm*—Fisher & Associates

[57] ABSTRACT

A fetal monitor is provided for gathering characteristic data such as fetal electrocardiogram, temperature and intra-uterine pressure so that fetal health may be determined during intra-operative and postoperative periods. The fetal monitor comprises a remote sensing unit, the remote sensing unit containing sensors which continually sample fetal temperature and electrocardiogram. A transceiver is housed in the remote sensing unit and outputs the sampled fetal temperature and electrocardiogram signals to an external antenna. A monitoring station is provided for monitoring the fetal temperature and electrocardiogram signals from the antenna. Additionally, a pressure transducer may be housed in the remote sensing unit for continually sampling intra-uterine pressure. This intra-uterine pressure signal in combination with the above signals are utilized to determine fetal health or the onset and progress of parturition.

2 Claims, 8 Drawing Sheets

B'METHOD FOR MONITORING FETAL CHARACTERISTICS BY RADIOTELEMETRIC TRANSMISSION

CROSS-REFERENCE TO RELATED APPLICATIONS

This application is a division of application Ser. No. 08/081,139, filed Jun. 25, 1993, now U.S. Pat. No. 5,431,171. This application makes reference to the following U.S. Applications. The first application is U.S. Appl. No. 08/081,133, entitled "Monitoring Uterine Contractions by Radiotelemetric Transmission", filed Jun. 25, 1993 now U.S. Pat. No. 5,373,852. This application is hereby incorporated by reference.

BACKGROUND OF THE INVENTION

1. Field of the Invention

The present invention relates generally to measuring devices, and more particularly to a measuring device that measures characteristics such as fetal electrocardiogram, temperature and intra-uterine pressure to determine fetal health during intra-operative and postoperative periods.

2. Description of the Prior Art

Improvements in obstetrical ultrasound have stimulated continuous improvements in a doctor's ability to treat congenital anomalies. In the past twenty years it has become possible to treat a fetus with a congenital anomaly in a progressively interventional fashion. Fetal cardiac arrhythmia's can be treated pharmacologically, see "Treatment of Fetal Arrhythmias," Wladimiroff & Stewart, Br. J. Hosp. Med. (1985). Fetal anemia can be corrected by intra-uterine transfusion of blood, see "Intrauterine Transfusion of Fetus in Hemolytic Disease," Liley, A. W., Br. Med. J., 5365: 1107–1109 (1963). Additionally, some fetal conditions are amenable to percutaneous catheter drainage, see "Catheter Shunts for Fetal Hydronephrosis and Hydrocephalus," Manning, Harrison & Rodeck, N. Eng. J. Med., 315: 336–340 (1986). Finally, there are some highly selected life-threatening fetal anomalies that can only be treated by hysterotomy and open surgical repair of the fetal defect. For example, bilateral urinary tract obstructions, congenital diaphragmatic hernia, and some types of fetal tumors have all been treated by open surgical repair. For further information on fetal surgical procedures, see "Early Experience with Open Fetal Surgery For Congenital Hydromephrosis," Crombleholme, Harrison & Langer, J. Pediatr. Surg., 23: 1114–1121 (1988); "Correction of Congenital Diaphragmatic Hernia In-Utero. V. Initial Clinical Experience," Harrison et al., J. Pediatr. Surg., 25: 47–57 (1990); "Successful Repair In-Utero of a Fetal Diaphragmatic Hernia After Removal of Herniated Viscera from the Left Thorax," Harrison et al., N. Eng. J. Med., 322: 1582–1584 (1990); "Fetal Hydrops and Death from Sacrococcygeal Teratoma: Rational for Fetal Surgery," Langer, Harrison & Schmidt, Am. J. Obstet. Gynecol., 160: 1145–1150 (1989); and "Antenatal intervention for Congenital Cystic Adenomatoid Malformation," Harrison, Adzick & Jennings, Lancet, 336: 965–967 (1990).

As may be seen from the above articles, the need for an accurate device for monitoring fetal health is vital for increasing the success rate of the above mentioned surgical procedures. The monitoring of the fetus is critical to fetal health care management and is also an aid in the monitoring of the onset of parturition. Thus, there are two critical periods for monitoring a fetus, 1) during intraoperative and postoperative periods as well as 2) during the onset of parturition.

The current techniques for monitoring fetal health include the monitoring of the fetal electrocardiogram during intraoperative periods or the use of ultrasound for postoperative periods. In both situations, there are significant drawbacks to these techniques.

During the intraoperative period, pulse oximetry, percutaneously placed electrical leads, and sterile intraoperative ultrasound are utilized for determining fetal cardiac function. These devices are generally designed for an adult and thus the sensitivity of the device is incapable of distinguishing the electrocardiogram signal of the fetus from that of the mother. Another problem with this type of device is the inability to secure the electrocardiogram leads, even with sutures. Additionally, these devices were designed to operate in a dry environment while the environment of the fetus is a fluid based environment. Thus, there is a problem with the electrical leads shorting and potentially burning or electrically shocking the fetus. In order to avoid this possibility, current techniques require the removal of the leads when the fetus is returned to the uterus. Thus, these techniques do not allow for continuous monitoring when the fetus is returned to the uterus and the hysterotomy is closed, a critical period of time when the umbilical cord may be kinked or the fetus may be compromised by poor positioning. Finally, fetal electrocardiography, pulse oximetry, and intra-operative ultrasound are cumbersome and the electrocardiography and pulse oximetry equipment have been unreliable in the past.

During the intra-operative period, the monitoring of fetal temperature is very important in the management of the fetus and the prevention of intraoperative hypothermia. Currently there are no devices which provide both fetal electrocardiogram and temperature signals.

During the postoperative period, the fetus may be monitored by electromagnetic or acoustical signals and a doppler effect thereon. For example, U.S. Pat. No. 3,606,879 (Estes) discloses an ultrasonic apparatus which is used for monitoring fetal heartbeat by detecting the change in frequency, due to a doppler effect, of an ultrasonic wave which passes through the fetus. Additionally, uterine contractions and cervical dilations are measured by the change in transit times of each pulse of ultrasonic energy. This doppler signal is intermittent and unreliable because of fetal movement and positioning, especially in the situation of fetal distress. The data from fetal doppler can be difficult to interpret. For example, a signal dropping in magnitude could mean either that the fetus has lost cardiac function or that the fetus has changed position. The use of real time ultrasound may only be performed intermittently, i.e., is limited by the availability of operator time to only once or twice per day. Other techniques such as fetal electrocardiogram (ECG) recordings across the maternal abdomen and fetal phonocardiography are ineffective with respect to fetus' because of the small signal to noise ratio. The use of fetal scalp ECG is not possible since the fetus is within the uterus with intact amniotic membranes.

As mentioned earlier, the second period for measuring fetal characteristics is during the onset of premature labor or parturition, child birth.

Each year in the U.S., 5% of all infants are born prematurely at an enormous cost to the health care system. Premature births account for 85% of neonatal deaths. About 10% of pregnant women in the U.S. are at risk or premature labor. Accurate detection or prediction of the occurrence of premature labor would allow the patient to be appropriately treated to suppress labor, thereby improving the chances that delivery will occur closer to term. The closer the delivery is to term, the lower the mortality rate and the lower the cost post-delivery neonatal care.

Several methods have been employed or proposed for detection or prediction of premature labor. These include both natural and instrument-based means.

Symptomatic self-monitoring is a natural means whereby the mother is educated in the symptoms of uterine contractions or cervical dilatation and receives regular counseling from a nurse. This approach has the advantage that it is non-invasive and inexpensive, since it can be done at home. However, it requires significant discipline, is time consuming for the patient, and lacks uniform accuracy. Mammary stimulation, cervical distensibility, and fetal breathing movements encompass other natural means. However, these methods require that the patient visit a care provider. They are therefore expensive and inconvenient.

Intrauterine pressure (IUP) measurement devices are considered to be the most accurate means available for measuring frequency of occurrence, duration, and intensity of uterine contractions. This technique has frequently been used to validate the accuracy of other methods of monitoring uterine activity. In this method a transvaginal catheter is inserted into the uterus. Open lumen fluid-filled catheters may be used, but require regular flushing to keep the lumen free of cellular debris. Catheters have been constructed with a balloon tip to eliminate the need for regular flushing. Microballoon-tipped catheters provide poor accuracy. Larger balloons provide better accuracy but their presence leads to irritation and artifactual stimulation to both the uterus and fetus. In addition, their use is restricted to bed-ridden patients and there is a risk of infection. Catheters that employ a solid state pressure transducer at the tip or fiber optic technology have also been used. Use of these techniques is generally limited to bed-ridden patients due to the risk of infection. An implantable pressuretelemetry device has also been used (Smyth, 1960) for monitoring intrauterine pressure. This device has been introduced into the uterine cavity external to the membranes to measure IUP following induction of labor. The authors suggest its use to "extending obstetric research and treatment control." No reference is made to using this device as a tool for prediction or detection or premature labor.

With the exception of symptomatic self-monitoring, use of the above methods has been restricted to a care providers office. However, successful treatment of preterm labor depends on early diagnosis (Iam, et. al., 1990) and these methods do not provide the timely information needed to effect prompt intervention and arrest labor. Methods suitable for monitoring patients as they go about their daily activities present a significant advantage in early diagnosis of preterm labor.

The guard-ring tocodynamometer provides a non-invasive means for monitoring uterine activity and represents the current state-of-the-art for detecting premature labor in ambulatory patients. This device is placed on the maternal abdomen and held in place by an elastic belt. It employs a "guard-ring" to flatten the abdomen within an area over which pressure applied to a sensing diaphragm by the abdominal tissues is sensed. Pressure measurements taken at this flattened area are representative of intrauterine pressures. Some commercially available tocodynamometers are capable of transmitting data to a clinic or doctors office via telephone lines. Studies of the effectiveness of these devices have demonstrated variable results.

In an attempt to provide doctors with accurate information on the condition of their patient during labor, many devices have been designed to detect both the onset of labor and the condition of the mother during the birthing process. The determination of the onset of labor is even more important when fetal surgery has been performed since preterm labor is a substantial problem associated with fetal surgery.

An example of one method for detection of parturition is the use of temperature sensors to detect temperature changes in a mother. U.S. Pat. No. 4,651,137 (Zartman) discloses an intravaginal parturition alarm and method for its use. The device comprises an anchor, a temperature sensor affixed to the anchor, and an alarm. During the onset of parturition, the anchor is displaced from an anterior portion of the female's vagina and is expulsed to a posterior portion of the vagina. The temperature sensor detects the change in temperature between the two vaginal regions and activates the alarm. As is obvious, this method is highly invidious.

Aside from the use of the temperature change upon expulsion of an object from the reproductive tract as an indicator of parturition, others have attempted without success to show a reliable relationship between temperature phenomena and the onset of parturition and related events. Research reports may be summarized as describing a body temperature increase during the latter part of pregnancy, with a substantial drop during the last few days to a few hours before parturition. However, for a number of reasons, the efforts of workers in the field to develop a reliable relationship between temperature phenomena and the onset of parturition have failed.

In fact the prior art would actually lead one away from the use of temperature measurements as a reliable tool in the forecasting and identification of occurrences related to parturition. Researchers in the field generally reported failures in their attempts to use such measurements in forecasting and determining occurrences related to parturition, thus dissuading other researchers from further study. Additionally, with only one exception, no current textbooks on reproductive physiology have been found that comment on any temperature phenomenon related to parturition.

Detection of parturition in animals has been accomplished in various ways. For example, U.S. Pat. No. 4,707,685 (Carrier et al.) discloses a system for detection of parturition which in effect is a continuity circuit. When a cow enters parturition, a thin wire, disposed about the animals vulva, is broken and thus continuity in an electric circuit is terminated. This lack of continuity sets off an alarm. U.S. Pat. No. 4,936,316 (Jewett) discloses the monitoring of the swelling of an animals vulva.

While significant efforts are made to monitor the mother, the other participant in the berthing process, i.e., the fetus, is generally ignored as a source for information. One vital sign which is measured is the fetal heartbeat. Physicians generally monitor the fetal heartbeat by using a stethoscope to determine the fetal condition. This method of fetal heartbeat monitoring is severely limited due to the shortcomings in the ability of an individual to instantaneously analyze the information transmitted to him and to detect suitable characteristics of the fetal heartbeat pattern.

The importance of continuous fetal heart rate monitoring and the shortcomings of evaluation by stethoscope are discussed in "An Introduction to Fetal Heartrate Monitoring" by Edward H. Hon M.D., published by the Postgraduate Division, University of Southern California School of Medicine. This publication also discusses problems associated with the monitoring of fetal heart rate caused by interference associated with uterine contractions during labor.

There has been an emergence of fetal monitoring devices which are utilized to monitor the status of the fetus during parturition. For example, U.S. Pat. No. 4,537,197 (Hulka) discloses a fetal oxygen monitor which is attached to the fetus' scalp after the onset of parturition, i.e, after the fetus' head is accessible through the vagina. The fetal monitor comprises a fetal scalp cap; a three channel catheter; two fiber optic bundles connected to the cap, one for transmitting light and the other for receiving light; and a oxygen level analyzer attached to the distal ends of the fiber optic bundles.

U.S. Pat. No. 3,989,034 (Hojaiban) discloses an apparatus for determining the heart rate of a fetus during labor. The device comprises a means for receiving a measured fetal heart rate signal; a means for receiving a uterus pressure signal; and a means for determining an actual fetal heart rate based upon the uterine pressure and the measured fetal heart rate.

U.S. Pat. No. 4,951,680 (Kirk et al.) discloses an apparatus for monitoring a fetus during labor. The apparatus comprises a scalp electrode for repeatedly deriving signals representative of the P-R interval of the fetal heart and the period of the fetal heartbeat; and a microprocessor for determining fetal health based upon the change in the above two signals.

None of these devices provide information on both fetal electrocardiogram and fetal temperature. Fetal temperature is an essential criteria to measure for determining fetal distress syndrome, which may occur before or during parturition. When fetal distress syndrome occurs, the fetus' temperature begins to climb dramatically, and the mother's temperature similarly undergoes a marked temperature increase. It is important to administer suitable treatment to remedy the problem as soon as possible in order to reduce the risk of fetal mortality or injury. For further information, please see: Weisz, "The Temperature Phenomenon Before Parturition and Its Clinical Importance," J.A.V.M.A. 102: 123 (1943).

The automatic administration of drugs based upon medical characteristics of the patient are utilized in areas such as high blood pressure treatment, blood oxygen concentration problems, and the treatment of diabetes. For example, U.S. Pat. No. 4,003,379 (Ellinwood) discloses a medication dispenser which is inserted into a patient's body and will dispense upon particular conditions being present. The dispenser comprises at least one sensor, control circuitry, a power source, a dispensing means, and medication storage means. Sensors and logic control circuitry are provided within the dispenser for measuring the existence or absence of a particular condition such as high blood pressure. The sensors may include 1) blood pressure detecting devices; 2) electrical activity from the carotid sinus or aortic body; 3) possible electrical activity from the sympathetic outflow; and 4) electrocardiogram.

U.S. Pat. No. 4,543,955 (Schroeppel) discloses a medical implant which includes a sensor assembly disposed remotely from the implant; signal converting circuitry for converting the signals from the sensor to a coded signal, a transmitting means for transmitting the coded signal, and an activation device for receiving the coded signal and actuating the activation device based upon the coded signal. The parameters sensed by this system are body temperature, blood oxygen concentrations or blood potassium concentrations.

U.S. Pat. No. 4,596,575 (Rosenberg et al.) discloses an insulin dispenser. The device comprises an implant having a transducer, an electronic control unit, a piezoelectric pump and an insulin reservoir. In operation, an external controller provides an actuation signal to the transducer which in turn sends an actuation signal to the electronic control unit. The control unit actuates the piezoelectric pump which in turn forces insulin to be dispensed from the reservoir.

While the prior art has appreciated the importance of suitably administering treatment to the mother and fetus upon the occurrence of fetal stress syndrome, the prior art has failed to adequately provide a means for detecting the onset of fetal stress syndrome and automatically administering the required treatment.

Although current technology is available for comparing measurements expressed in quantitative form with quantitative tolerance limits and signaling when those limits are exceeded and activating a device for the administration of medication based upon this information, the evaluation of the fetal condition has, until now, often been a qualitative one beyond the capabilities of the known state of the art identified above. Additionally, the prior art does not provide any teachings for continuously monitoring a fetus before the onset of parturition. This monitoring would be vitally important in cases where fetal surgery has been performed.

SUMMARY OF THE INVENTION

It is therefore an object of the present invention to provide a fetal monitor which will provide accurate information on the fetal health during intra-operative and postoperative periods.

It is a further object to provide a fetal monitor which is directly attached to a fetus during fetal surgery.

It is yet another object to provide a fetal monitor which eliminates the possibility of electrical shock and short circuits.

It is yet another object to provide a method for implanting the electrical leads of the fetal monitor to accomplish the goal of eliminating short circuits.

It is yet another object to provide a means for the accurate detection of fetal temperature and electrocardiogram as well as maternal intra-uterine pressure.

In a second embodiment, it is an object to provide a fetal monitor for accurately determining the onset of parturition.

It is a further object to provide a means for the accurate detection of fetal temperature and electrocardiogram as well as maternal intra-uterine pressure, electromyogram and temperature of the uterus.

In a third embodiment, it is an object to provide a fetal monitor which may be used to collect data over conventional communications lines.

In all of the above embodiments, it is an object to provide an antenna which provides invidious monitoring of the fetus during intra-operative and postoperative periods as well as during the onset of parturition.

Finally, it is an object of the invention to provide a fetal monitor which may automatically dispense medication upon the existence of particular medical conditions.

According to one broad aspect of the present invention, there is provided a fetal monitor comprising a means for continually sampling the temperature of the fetus and for outputting a sampled temperature signal; a means for continually sampling the electrocardiogram of the fetus and for outputting a sampled electrocardiogram signal; and means for receiving said fetal temperature and electrocardiogram signals and for determining the fetal health based upon the sampled temperature and electrocardiogram signals.

According to another broad aspect of the invention, there is provided a fetal monitor further comprising a uterine monitor. The uterine monitor comprises a means for continually sampling the temperature of a mother and for outputting a sampled maternal temperature signal; a means for continually sampling the electromyogram of a mother's uterus and for outputting a sampled maternal electromyogram signal; and means for receiving said maternal temperature and electromyogram signals and for determining the existence of fetal conditions based upon said sampled maternal temperature, maternal electromyogram, fetal temperature, and fetal electrocardiogram. Additionally, a means for continually sampling intra-uterine pressure and for outputting a sampled intra-uterine pressure signal may be provided. This intra-uterine pressure signal in combination with the above signals are utilized to determine the onset and progress of parturition.

Other objects and features of the present invention will be apparent from the following detailed description of the preferred embodiment.

BRIEF DESCRIPTION OF THE DRAWINGS

The invention will be further described in conjunction with the accompanying drawings, in which.

DETAILED DESCRIPTION OF THE PREFERRED EMBODIMENT

Figure 1:
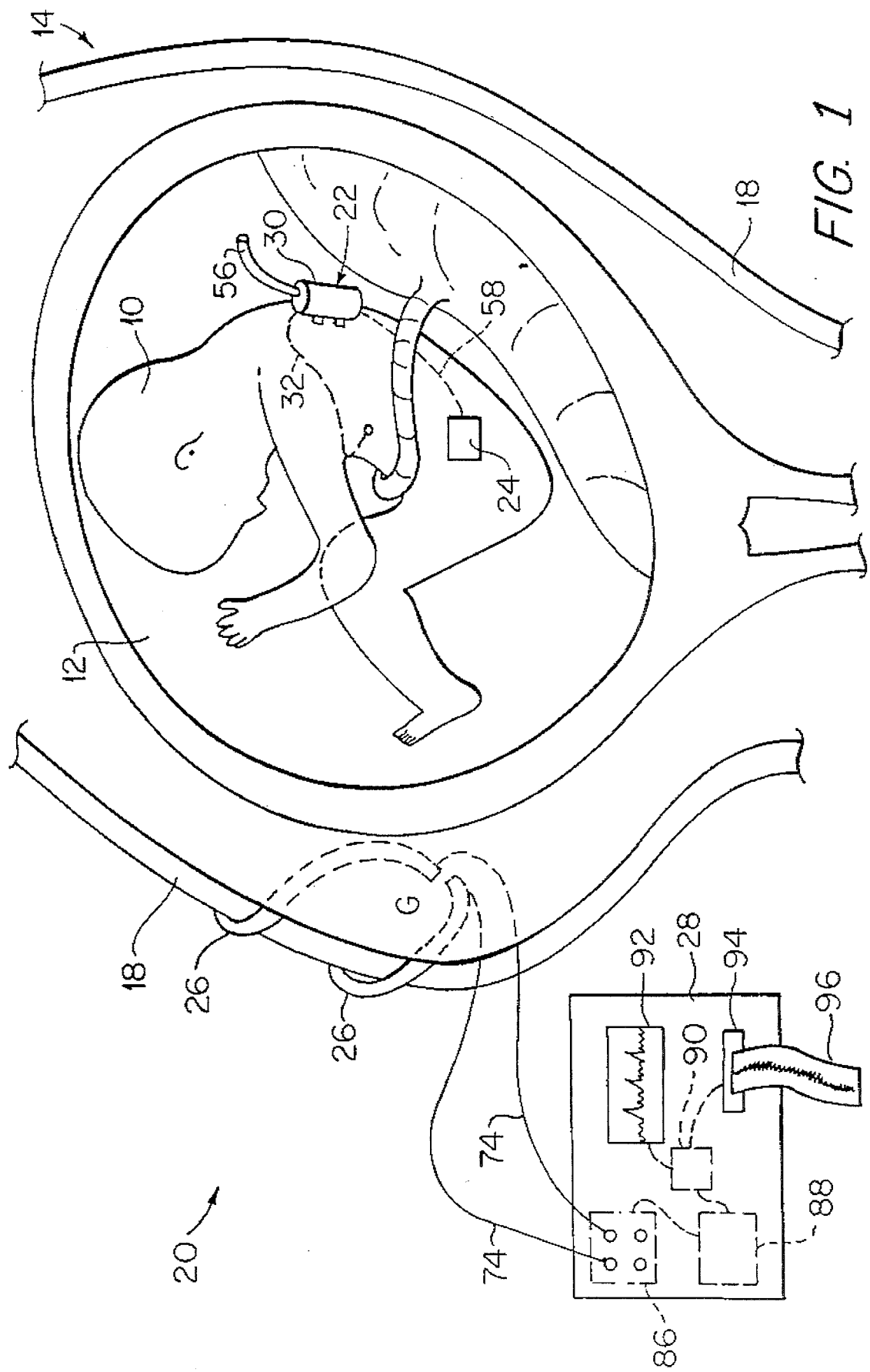
FIG. 1 is a cross sectional view of a fetus in a uterus having an attached fetal monitoring and medication delivery system constructed in accordance with a preferred embodiment of the invention.

With reference to the figures, wherein like reference characters indicate like elements throughout the several views and, in particular, with reference to FIG. 1, a fetus 10 is disposed within the uterus 12 of a mother 14. The uterus 12 is defined by a uterine wall 16 which is located within the abdomen 18 of the mother 14. A fetal monitoring system, generally denoted 20, is provided to monitor the status of fetus 10 during an intra-operative or postoperative period. The fetal monitoring system 20 comprises an implantable remote sensing unit 22, a medication dispenser 24, an antenna 26, and a monitor 28.

Remote Sensing Unit

The remote sensing unit 22 is a remote sensing device which detects fetal temperature and electrocardiogram. The remote sensing unit 22 may also detect intra-uterine pressure by a pressure transducer 30. The remote sensing unit 22 is secured to the fetus 10 by at least one electrocardiogram lead 32. This lead is surgically inserted under the skin of the fetus 10 and will be discussed in detail below.

Figure 2:
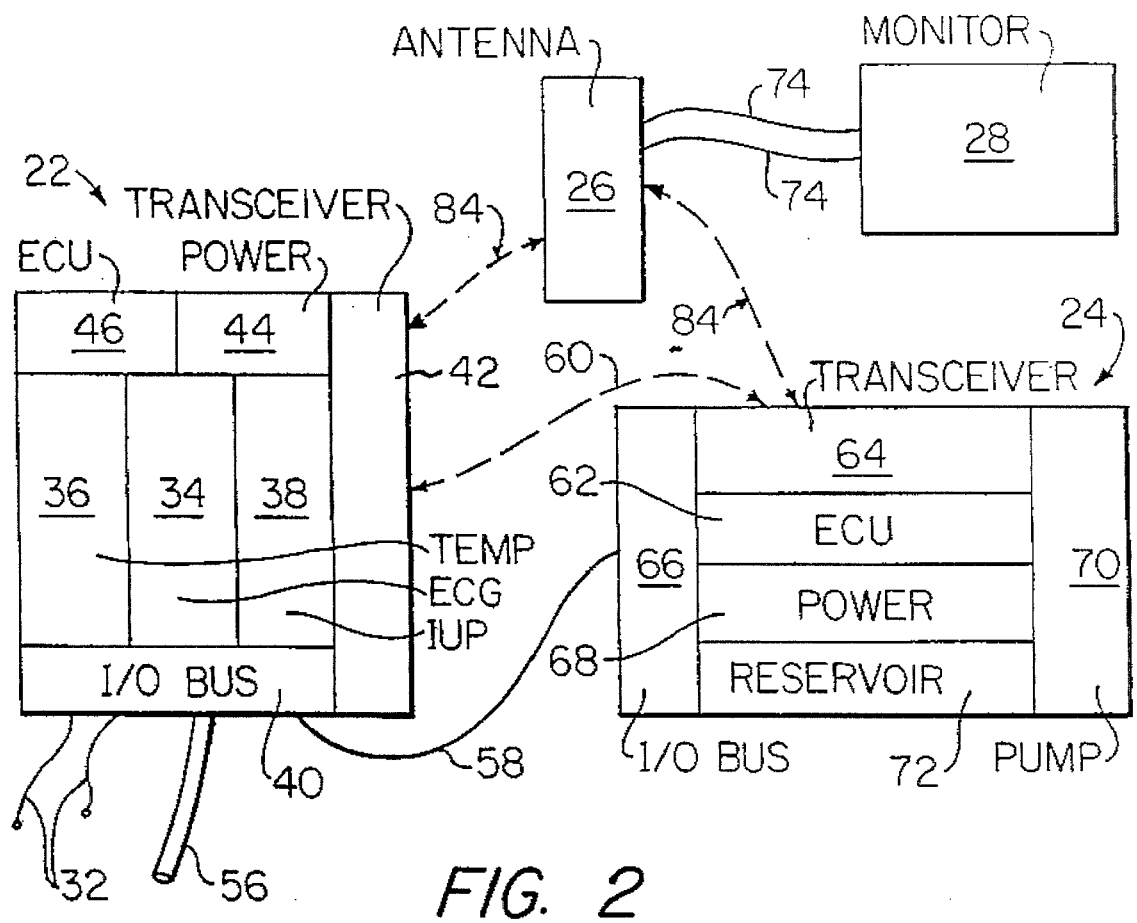
FIG. 2 is a block diagram of the components of the fetal monitor and medication delivery system of FIG. 1.

Referring to FIG. 2, a block diagram of the major components of remote sensing unit 22 are illustrated. As may be seen, circuitry for an electrocardiogram (ECG) 34, a temperature (Temp) sensor 36 and an intra-uterine (IUP) 38 sensor are provided within remote sensing unit 22. Information is transmitted to and from sensors 34, 36 and 38 via an input/output (I/O) bus 40. I/O bus 40 also provides communication between a transceiver 42 and sensors 34, 36 and 38. Power is supplied by a conventional power source 44 such as a silver oxide battery or any other power source known in the art. An electronic control unit (ECU) 46 is provided for controlling the power supply to sensors 34, 36 and 38 as well as communication through I/O bus 40 and transceiver 42. Each of the components of the remote sensing unit 22 will be described in detail below.

Figure 3A:
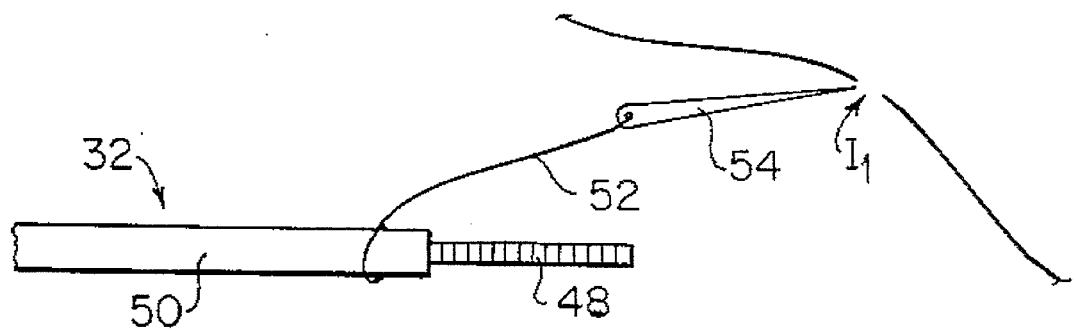
FIG. 3A is side elevational view of an electrocardiogram lead utilized in conjunction with the fetal monitor of FIG. 1.

The electrocardiogram sensor 34 includes at least one electrocardiogram lead 32 which is affixed at a proximal end to a conventional signal processing circuit and at the distal end to the fetus 10. In the preferred embodiment, there are two electrocardiogram leads 32, the first affixed to the posterior and the second to the anterior chest cavity of fetus 10. Referring to FIG. 3A, an electrocardiogram lead 32 is illustrated. The electrocardiogram lead 32 is formed from an inner conductive material 48 having a distal tip portion 49 and an outer insulative sheathing 50 which surrounds conductive material 48. The distal tip portion 49 of conductive material 48 is exposed to allow for an electrocardiogram signal to be transmitted along lead 32.

In conventional electrocardiogram leads, this distal tip portion 49 is left exposed to the environment. Having an exposed tip portion 49 creates significant problems when lead 32 is used in fetal monitoring. This exposed tip portion 49 may short-circuit the electrical circuit attached to the proximal end of lead 32 since lead 32 may be exposed to amniotic fluids which are maintained within the uterus 12.

This invention contemplates a method for surgically installing lead 32 to prevent the possibility of a short circuit or electrical shock and is described with reference to FIGS. 3A and 3B. As may be seen in FIG. 3A, a suture or other thin filament 52 is attached to the distal end of lead 32 just before the exposed tip portion 49. Affixed to the other end of suture 52 is a needle 54. Next, an incision or $I_1$ is made in the posterior abdominal wall of fetus 10. Incision $I_1$ is wide enough to allow needle 54, suture 52 and the entire lead 32 to enter fetus 10. Then, needle 54 is positioned so as to thread lead 32 under the skin to the anterior abdominal wall of fetus 10. A second incision or needle hole $I_2$ is made to allow needle 54 to be removed from fetus 10. Incision $I_2$ is only wide enough to allow needle 54 and suture 52 to exit fetus 10.

Figure 3B:
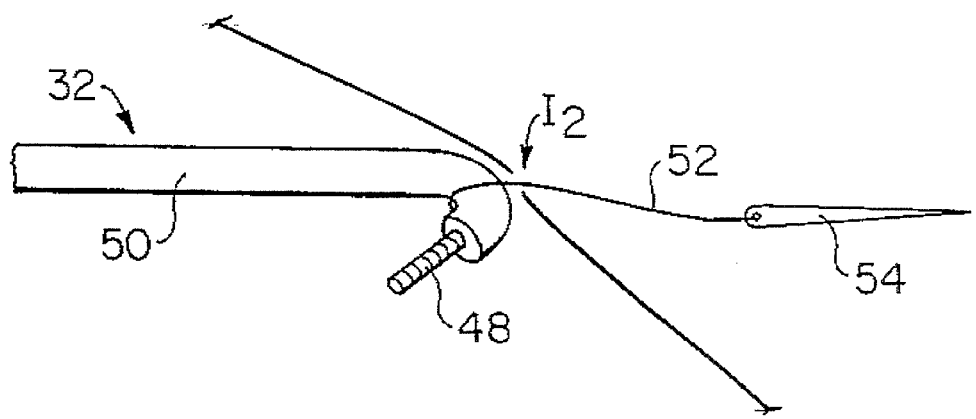
FIG. 3B is a side elevational view of the electrocardiogram lead of FIG. 3A as installed by the preferred method of the invention.

As may be seen in FIG. 3B, the conductive tip 48 is prevented from exiting incision $I_2$ because its diameter exceeds that of incision $I_2$. Finally, incision $I_2$ may be sealed by suture 52 in a conventional fashion. Thus, the entire lead 32 is maintained subcutaneously and is prevented from coming into contact with the amniotic fluid. This method of subcutaneously implanting the lead 32 reduces the risk of a short-circuit as well as that of electrical shock. While in a preferred embodiment the incision $I_1$ and $I_2$ are made in the respective posterior and anterior abdominal walls, it is within the contemplation of this method to provide any entry and exit point for needle 54.

In a similar fashion, the above process is repeated for positioning and securing each lead 32 to fetus 10. After all leads are secured, remote sensing unit 22 is attached to the proximal ends of each respective lead 32 and thus remote sensing unit 22 is firmly secured to the outer layer of skin of the fetus 10 by leads 32 or conventinal sutures and suture tabs. Electrocardiogram data is gathered in a conventional fashion and may be in either analog or digital form.

The temperature sensor 36 and associated signal processing circuit are an integral part of remote sensing unit 22. The sensor 36 is maintained in contact with the outer layer of skin of fetus 10 by remote sensing unit 22 and associated leads 32. Temperature information is gathered in a conventional fashion and may be in either analog or digital form. In an alternative embodiment, the above described temperature sensor 36 will utilize a sensor which is disposed remotely from remote sensing unit 22. The prior art has tailed to provide accurate temperature measurements of fetus 10 during the intra-operative or postoperative periods.

The importance of intra-operative monitoring of fetal temperature was demonstrated during human fetal surgery operations which were conducted in conjunction with testing remote sensing unit 22. The rate at which fetal temperature fell after fetus 10 was exposed to ambient air was alarmingly quick. In less than 10 minutes, the fetal temperature dropped to dangerously low levels and was accompanied with a slowing in fetal heart rate. Thus, the quick and accurate monitoring of fetal temperature is essential in detecting and preventing the onset of fetal hypothermia.

Additionally, the monitoring of fetal temperature during the postoperative period is important in determining the onset of fetal distress as well as the onset of parturition.

The pressure sensor 38 comprises a pressure transducer 30 and an electronic circuit for signal processing, both of which are located within remote sensing unit 22. Additionally, a pressure transmission catheter 56 is disposed externally to remote sensing unit 22 and is connected thereto for providing fluid communication between transducer 30 and uterus 12. It should be appreciated that a solid state pressure sensor such as that used in pressure sensing pacemakers which measure incremental changes in pressure with respect to time, i.e., dp/dt, as well as instantaneous pressure may be utilized in place of the sensor 38, described above. This will eliminate the need for the pressure transmission catheter 56 and thus reduce the problem of sterilizing the equipment. Additionally, it should be appreciated that a dual lumen catheter, such as that produced by Data Sciences of Minnesota, which utilizes pressure transducer 30 and a gel, may be employed. This structure has the advantage of maintaining accurate measurements without requiring periodic flushing. Finally, fiber optic, capacitance, semiconductor strain gage, or any other type of pressure measuring device may be employed in sensing unit 22 in place of pressure transducer 30.

An I/O Bus 40 is provided for allowing for interoperability between sensors 34, 36 and 38 and transceiver 42. In a preferred embodiment, I/O bus 40 will be a simple one way communications line having buffers for data storage. It should be appreciated that a more complex I/O bus may be used in conjunction with a complex ECU 46 for providing additional features such as duplex communication, multiplexing or encoding. In a preferred embodiment, the I/O bus will have a communications line 58 for allowing information from sensors 34, 36 and 38 as well as control information from ECU 46 to be relayed to medication dispenser 24. Communications line 58 may be a standard copper wire or fiber optic cable, it should be appreciated that communication between remote sensing unit 22 and medication dispenser 24 may be accomplished by radiotelemetry signal 60 between respective transceivers 42 and 64. This radiotelemetry signal is indicated in FIG. 2 as dashed line 60.

As mentioned above, remote sensing unit 22 contains a transceiver 42. Transceiver 42 is a combination of a radio transmitter and receiver which is maintained in a common housing and employs common circuit components for both transmitting and receiving radio signals. In a preferred embodiment, the bandwidths of the radio signals are within that of traditional radio-telemetry devices. As mentioned above, the transceiver 42 receives sensor data from the I/O bus 40 and then in turn transmits this sensor data to either an external antenna 26 or to a medication dispenser 24. It should be appreciated that any frequency band may be employed for the transceiver so long as each band is unique to each particular transceiver 42. This is vitally important since there may be more than one patient being monitored at any one time. Additionally, in an alternative embodiment, the frequency band used to communicate with the medication dispenser 24 will be different from that of the antenna 26. As may be seen, communication between remote sensing unit 22 and medication dispenser 24 may be conducted via a radio transmission channel indicated by dashed line 60 or by a more conventional communications line 58.

Power is provided to the above components by a conventional power source 44. It should be appreciated that since the normal term of a mother 14 is approximately nine months, the power source 44 should be able to provide continuous power to the above systems for that time period. Currently, silver oxide batteries are utilized which provide power for at least four months. Power distribution may be controlled by the ECU 46 so that sensors 34, 36 and 38 may be selectively actuated when required and thus conserving the power supply from source 44.

The ECU 46 may be a conventional microcontroller which controls the communication along I/O bus 40 and power distribution as described above. For example, a known controller such as that described in Med. Progr. Technol. 9, 17–25 (1982) may be utilized. Additionally, the microcontroller may be modified by preprogramming it to automatically respond to particular characteristics which are detected by sensors 34, 36 and 38. In this case, the microcontroller may activate medication dispenser 24 to allow for treatment to be automatically delivered.

All external components of the remote sensing unit 22 will be coated with a thin layer of silicon or encased in a biocompatible case to allow for biocompatibility between the unit and fetus 10. This reduces the possibility of infection or rejection of remote sensing unit 22 by fetus 10.

Medication Dispenser

Turning now to the medication dispenser 24, as illustrated in FIG. 2, the major components of the medication dispenser 24 may be seen. The medication dispenser 24 comprises an electronic control unit (ECU) 62, a transceiver 64, an I/O bus 66, a power supply 68, a pump 70, and a medication reservoir 72. Elements 62, 64, 66, and 68 correspond to elements 46, 42, 40, and 44 respectively and function similarly. Therefore, only the differences in these elements will be discussed below.

As mentioned above the ECU 62 is similar to that of ECU 46. It should be appreciated that either ECU 46 or 62 is capable of automatically responding to particular characteristics which are detected by sensors 34, 36 and 38. Thus, if one ECU is provided with this feature, the other may have this feature deactivated. Alternatively, a comparator circuit may be provided to determine if both ECUs 46 and 62 agree on the response to the particular condition. In that case, medication dispenser 24 will only be activated if both ECUs 46 and 62 agree. Otherwise, an error signal will be sent to monitor 28 via antenna 26. Another major difference between ECUs is that ECU 62 will have to determine which reservoir 72 to physically connect to pump 70. This may be accomplished via conduits and electromagnetically controlled valves or any other valve means known in the art.

Pump 70 is preferably a piezoelectrically driven micropump generally similar to that described by Rosenberg et al. in U.S. Pat. No. 4,596,575. The major difference between the pump of this invention and that of Rosenberg is the location of the pump. Rosenberg contemplates the pumping of insulin into an adult patient. As is obvious, there are significant differences between and adult patient and fetus 10. One major consequence of the difference between patients is the need for accurate measurements of dispensed medication. Therefore, the sensitivity of pump 70 must be greater than that of Rosenberg. In the preferred embodiment, the pump 70 will only be required to dispense liquid medication. In an alternate embodiment, pump 70 may be modified to allow for dispensing of sold or powdered medications as well as liquids.

Finally, at least one reservoir 72 is provided for maintaining the medications. In a preferred embodiment, each reservoir 72 comprises a collapsible bag which is maintained within a rigid housing of medication dispenser 24.

As mentioned earlier, data from sensors 34, 36 and 38 are provided to medication dispenser 24 by remote sensing unit 22 via either a communications line 58 or a radio transmission channel 60. In an alternative embodiment, medication dispenser 24 will be provided with independent data sensors. All external components of medication dispenser 24 will be coated with a thin layer of silicon to allow for biocompatibility between dispenser 24 and fetus 10. This reduces the possibility of infection or rejection of medication dispenser 24 by fetus 10.

It should be appreciated that no known references have suggested the direct medical treatment of a fetus 10 by an automatic medication dispenser 24. The risk associated with such a device would generally exceed its practical use. But with the onset of fetal surgery, the benefit of such a device may far exceed the risk to fetus 10. This is due to the generally poor health of fetus 10 combined with the potential trauma caused by fetal surgery. Thus, the ability to monitor the health of fetus 10 in combination with the automatic delivery of medication directly to fetus 10 has come of age.

While the prior section has discussed the gathering of data and the value of this data, the next section shall discuss how that data is transmitted and manipulated in devices located outside of the mother 14.

Antenna

Figure 4B:
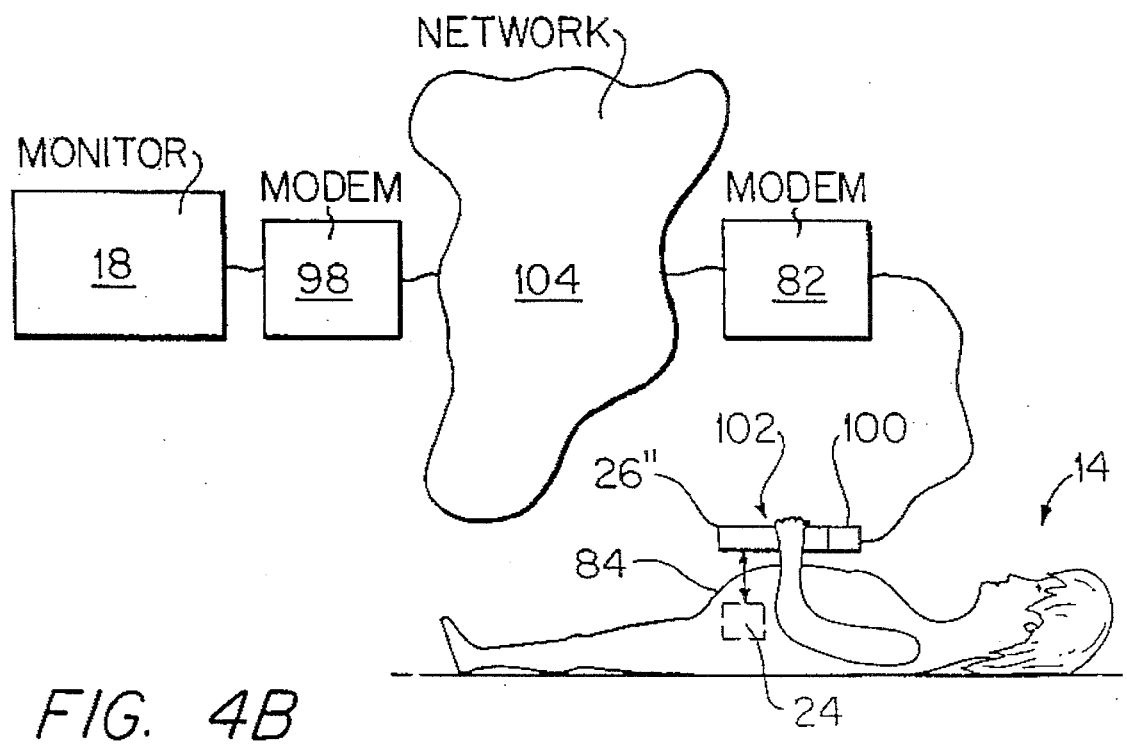
FIG. 4B is a block diagram of an alternate communications method utilized in conjunction with the fetal monitor of FIG. 1.
Figure 4C:
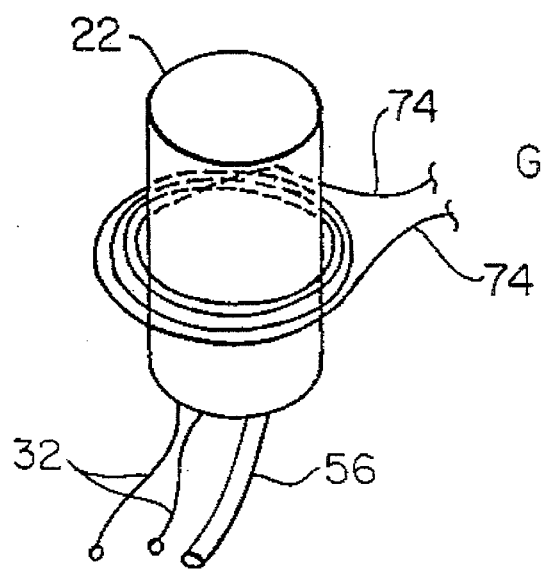
FIG. 4C shows a sensing unit attached to a wire lead.
Figure 4A:
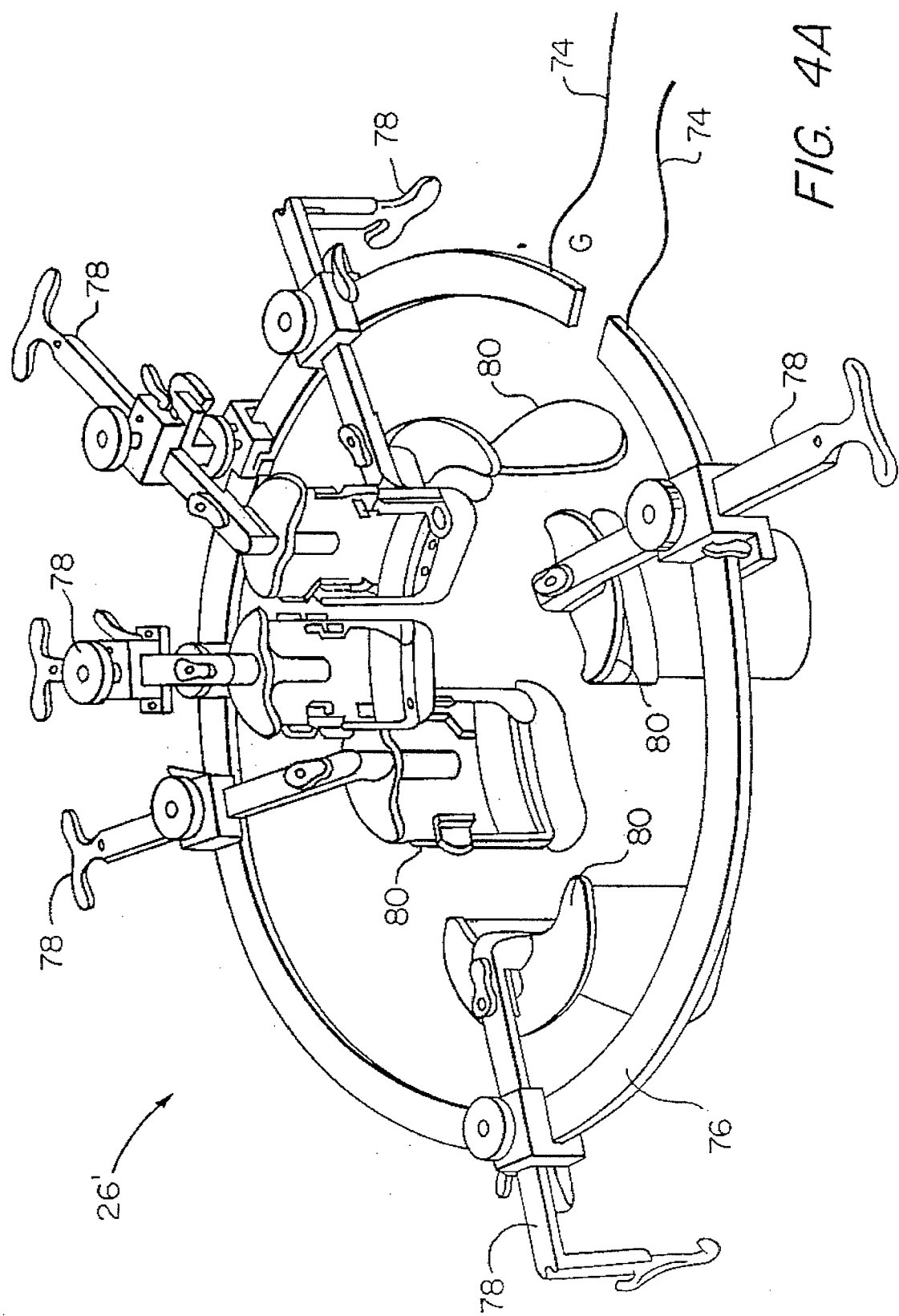
FIG. 4A is a plan view of an alternate embodiment of a ring antenna utilized in conjunction with the fetal monitor of FIG. 1.

As mentioned earlier, the ECG, temperature and intrauterine pressure information is transmitted from transceiver 42 by the use of a standard radio-telemetry signal 84 to an external monitor or control unit 28. This is accomplished by the radio-telemetry signal 84 being received by an antenna 26. There are three types of antennas 26 which are specifically contemplated by the invention. The first type of antenna 26 is a flexible loop antenna and is illustrated in FIG. 1 as element 26. The second type of antenna is a ring retractor antenna and is illustrated in FIG. 4A as element 26'. The third type of antenna is a wand or tubular antenna and is illustrated in FIG. 4B as element 26". The fourth type of antenna is a small contact loop antenna attached directly to the sensing unit 22 and is illustrated in FIG. 4C as element 26'''. Each of these antennas 26, 26', 26" and 26''' shall be discussed in detail below.

The flexible loop antenna 26 is formed from a conductive ring or band of material which is placed around the abdominal wall 18 of the mother 14. In a preferred embodiment, loop 26 will be formed from several conductive rings or bands which are interwoven. This may be more clearly pictured as several coils of wires which are compressed together. As may be seen in FIG. 1, a gap G is provided in the last coil of loop 26 to allow for a continuous electrical circuit to be formed between loop antenna 26 and monitor 28. Electrical leads 74 are attached to respective ends of gap G and are provided to allow an electrical connection between antenna 26 and monitor 28. For clarity only two electrical leads 74 have been illustrated in FIGS. 1, 2 and 4A. It should be appreciated that the number of electrical leads 74 will correspond to the number of monitored characteristics or sensors utilized in the fetal monitoring system 20. In a multiplexed system, there will only be one electrical lead 74. This ring structure is the preferred antenna 26 structure for both intra-operative and postoperative periods since the antenna 26 is capable of receiving a signal from any position within the mother 14, i.e., omnidirectional. Additionally, the antenna 26 may be bent to any shape, due to the mallable nature of the conductive rings, and thus may be bent to conform to the shape of the mother's abdomen 18.

The ring retractor antenna 26' which is illustrated in FIG. 4A comprises a conventional ring retractor such as that disclosed by Gauthier in U.S. Pat. No. 4,010,741. The conventional ring retractor is modified by providing a gap G in a conductive ring 76 for allowing a continuous electrical circuit to be formed between ring retractor antenna 26' and monitor 28. Electrical leads 74 are attached to respective ends of gap G for providing an electrical connection between antenna 26' and monitor 28. Additionally, there are a plurality of arms 78, each of which is secured to ring 76 and supports an associated retractor 80. The ring retractor antenna 26' functions in a similar fashion to a conventional ring retractor but also provides the ability to receive sensor information from transceivers 42 and 64 via radio-telemetry signal 84. This antenna 26' has the advantage of not increasing the number of additional devices which are present during an operation and thus, is the best choice for intraoperative monitoring. For best results, antenna 26' is used in conjunction with antenna 26 to receive an accurate radio-telemetry signal from transceivers 62 and 64.

In a similar fashion as loop antenna 26, a small contact loop antenna 26''' is illustrated in FIG. 4c. This contact antenna 26''' is fastened in a similar manner as loop antenna 26 except it is much smaller in size, i.e, approximately 1–2 cm diameter loop. The contact antenna is designed to be used during an interoperative period and is placed around and in contact with sensing unit 22. The antenna 26''' is attached to a wire lead 74 which is attached to monitor 28.

Finally, a wand or finger antenna 26" may be utilized in particular circumstances. The finger antenna 26" is a unidirectional antenna and thus is more limited than the flexible loop antenna 26. Antenna 26" is useful for postoperative monitoring of both fetus 10 and mother 14. In a preferred embodiment, this finer antenna 26" is provided with an RJ-11 jack and associated signal processing circuitry at a distal end to allow antenna 26' to be attached to a conventional modem 82. Thus, while a mother 14 is at home, her doctor may receive sensor information at a remote site such as a hospital or office. This communication system is discussed in greater detail below.

It should be appreciated that a combination of the above antennas may be utilized to provide the best data signal to monitor 28. Additionally, the purpose of antenna 26", illustrated in FIG. 4, may be achieved by using either antenna 26, 26' or 26''' in place of antenna 26". Finally, it should be appreciated that any known antenna which may receive frequencies in the frequency ranges of conventional radiotelemetry devices may be utilized in place of any of the above identified antennas.

Monitor

Turning back to FIGS. 1 and 2, a generic monitor 28 is illustrated. Monitor 28 includes a signal input means 86; a receiver 88 for processing the signal from input means 86; a computing means 90; and output means for visual or printed displays 92 and 94, respectively. In a preferred embodiment, the signal input means 86 is a patch panel which utilizes standard banana connectors affixed to electrical leads 74. Signals from input means 86 will be processed by a receiver, model CTR-86-SA-OPO7 and model BCM-100 consolidated matrix, produced by Data Sciences and distributed by Mini-Mitter Co. of Sunriver, Oreg. Early trials utilized a CTR-86 which had only electrocardiogram or electromyogram and temperature outputs. The signal output was an analog ECG or ECM and a voltage which corresponded to the temperature. The computing means 90 was Hewlett-Packard Vectra Model 50 which is produced by Hewlett-Fackard Co. of Sunnyvale, Calif. The computing means 90 further comprises a 10 MHz 80287 math coprocessor produced by Intel Corp. of Hillsboro, Oreg. and a DQ-1088 data acquisition card produced by Data Sciences, Inc. of St. Paul, Minn. Unfortunately this device was exceedingly clumsy and unreliable.

In a preferred embodiment pressure measurements are also taken. The transmitted multiplexed signal, i.e. the ECG, temperature and pressure is received by any of several antennas 26 described above and decoded by one of several receivers produced by Data Sciences, e.g., RIA 3000. Further signal processing and digital to analog conversion is performed by a DL10 decoder with analog (voltage) outputs by A10, A11 and A12 options. These analog signals are then processed by the computing means 90, e.g., a Macintosh 950 computer. The computing means 90 is also equipped with a National Instruments NB-M10-16 I/O board and a national Instruments NB-DMA 2800 interface board.

A computer based data acquisition system software package LabView, Version 2.2.1, is operated within computing means 90 for manipulating the data to determine the health of mother 14. This software package has been specifically modified to detect conditions such as fetal distress, hypothermia, and the onset of parturition. The application of these modifications are discussed below in conjunction with the overall operation of the fetal monitor 20.

Output from the computing means 90 may be displayed on a visual display means 92 such as a cathode ray tube (CRT), liquid crystal display or any other display means known in the art. Additionally, output from computing means 90 may be displayed on a strip chart recorder 94 such as Model MT 9500-OR produced by Coulbourn Instruments of Lehigh Valley, Pa. This strip chart recorder 94 allows for the simultaneous real time display of fetal temperature and recording of analog fetal electrocardiogram on a strip chart 96.

Additionally, a continuous real time display 92 of the electrocardiogram signal may be displayed on a Lifepak Six produced by Physio-Control, of Redmond, Wash.

Uterine Monitor

Figure 5:
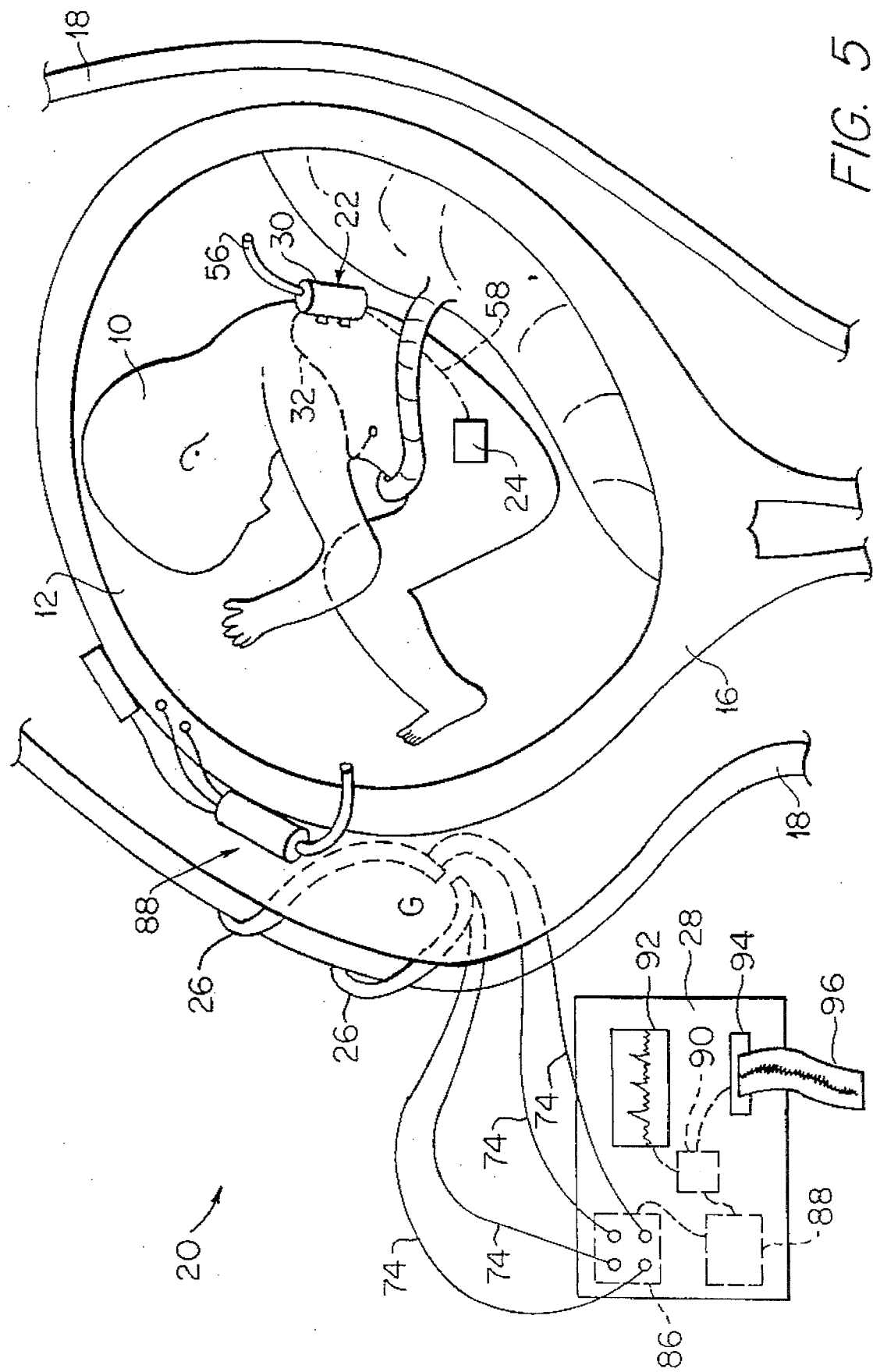
FIG. 5 is an alternate embodiment of the fetal monitor of FIG. 1.

Referring to FIG. 5, an optional uterine monitor 88 is illustrated in conjunction with the fetal monitor 20. Uterine monitor 88 provides information such as intra-uterine pressure, uterine temperature, and maternal uterine electromyogram to monitor 28. For a complete discussion of the uterine monitor 88, please see copending U.S. Appl. No. 08/081, 133, which is hereby incorporated by reference.

Operation of Device

Turning now to the operation of the fetal monitor 20 in conjunction with the uterine monitor 88, reference is made to FIGS. 6A, 6B, 7, 8, 9, and 10A–10D. As stated earlier, fetal monitor 20 is designed for use during intra-operative and postoperative periods as well as during the onset of parturition.

Figure 6A:
FIG. 6A is a plot of maternal electrocardiogram versus time.
Figure 6B:
FIG. 6B is a plot of fetal electrocardiogram versus time.
Figure 7:
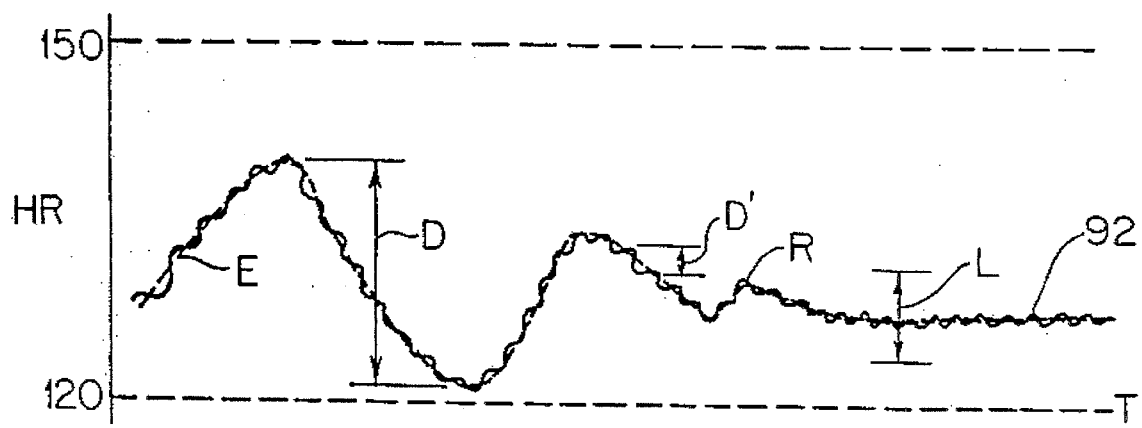
FIG. 7 is a plot of fetal heart rate versus time.
Figure 8:
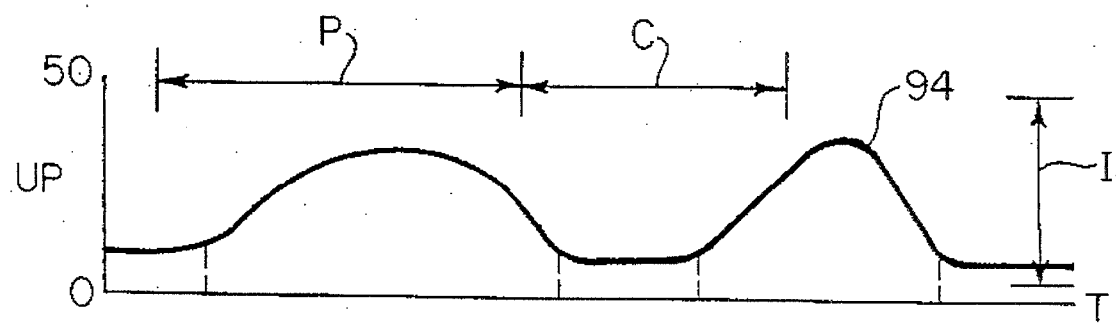
FIG. 8 is a plot of intrauterine pressure versus time.
Figure 9:
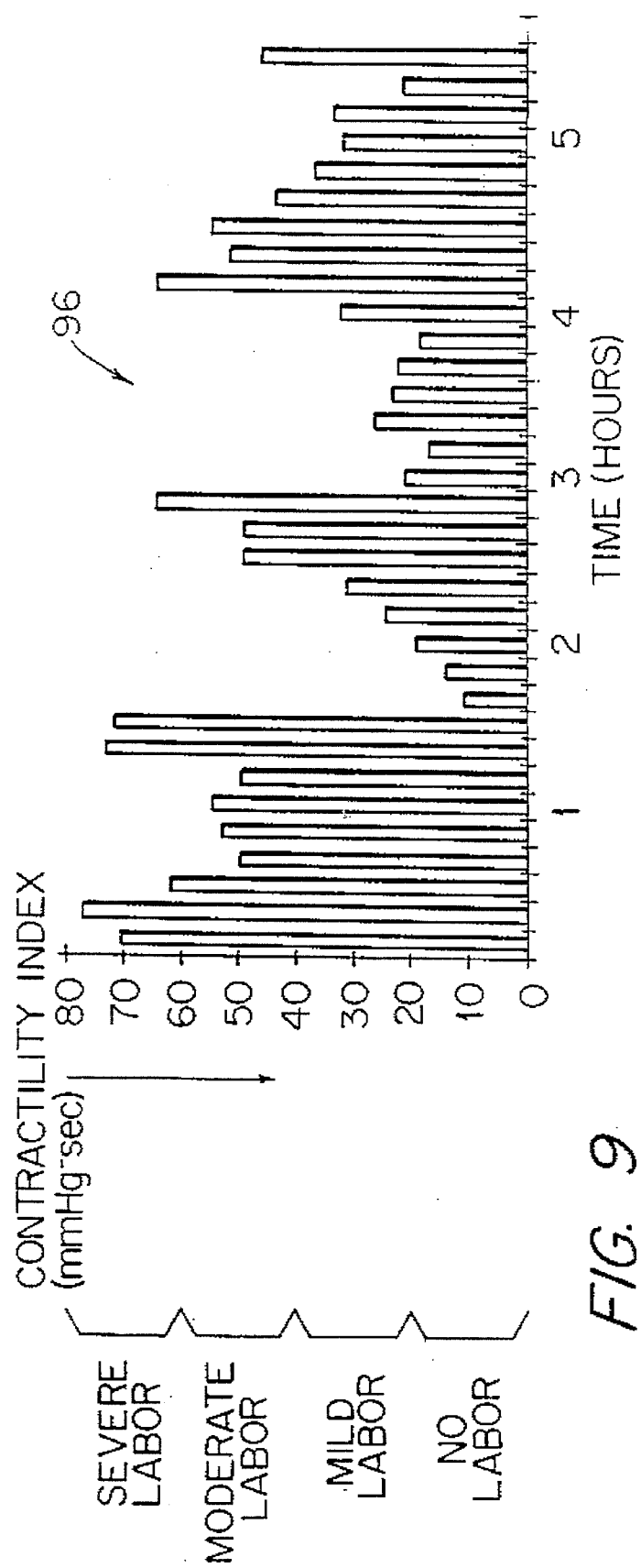
FIG. 9 is a plot of uterine contractility index versus time.

During the intra-operative and postoperative periods, the fetal monitor 20 will monitor a fetal electrocardiogram signal 90 as illustrated in FIG. 6B, as well as a fetal heart rate, generally denoted 92 in FIG. 7. The electrocardiogram signal 90 is first detected by electrocardiogram leads 32. These leads 32 relay signal 90 to electrocardiogram sensor 34 which in turn provides signal processing such as noise reduction and amplification to signal 90 as described above. Signal 90 is then transmitted by transceiver 42 to antenna 26 or transceiver 64 as described above. Once signal 90 is received by antenna 26, signal 90 is then transmitted to monitor 28 via electrical leads 74. Based upon the electrocardiogram signal 90, i.e, the period between consecutive beats, the fetal heart rate variability may be determined as illustrated in FIG. 7.

The fetal heart rate variability is an indicator of fetal distress. As may be seen from FIG. 7, heart rate variability has both long term and short term characteristics. The long term characteristics are represented by the envelope D of heart rate 92 and the short term characteristics being shown by the ripple R about the envelope E. Envelope E represents a straight line approximation of the actual heart rate 92. In a preferred embodiment, fetal distress is determined from the weighted average of the peak to peak distance D in the instantaneous heart rate 92, i.e. long term variability in heart rate. Alternatively, distress may be determined by the variability in short term heart rate as indicated by the distance D'. Finally, distress may be determined if predetermined minimum peak to peak limits L are not exceeded within a given period of time. It should be appreciated that a combination of the above methods may be employed. Since the fetal heart rate is affected by outside forces, such as contractions or fetal movement, the heart rate by itself is not a completely reliable indication of fetal distress. Thus, fetal temperature is also measured in a similar fashion to that described for the electrocardiogram.

This temperature data is vital for determining the onset of hypothermia and for providing collaborative evidence of fetal distress. Fetal temperature will vary with time between upper and lower acceptable temperature limits. By measuring the temperature and determining when the temperature falls below preset limits, hypothermia may be determined quickly and automatically. Additionally, by seeing if there is a temperature variation in conjunction with a heart rate variation, fetal distress may be accurately determined.

Turning now to monitoring the fetus during parturition, the measurement of fetal temperature and electrocardiogram as well as maternal temperature, intra-uterine pressure and electromyogram provide an accurate indication of the onset and progress of parturition and fetal health during this time.

During the onset of parturition, the uterine monitor 20 will monitor a maternal electromyogram signal 91 as illustrated in FIGS. 10A through 10D and may monitor maternal heart rate. During parturition, muscles in the uterine wall generate ion fluxes during cell depolarization which in turn lead to cellular contractions. This may be detected as changes in voltage across a portion of the muscle and is generally called an electromyogram. The voltage detected corresponds to a muscular contraction. The electromyogram signal 91 is first detected and utilized in a similar fasion as the fetal electrocardiogram signal 90. It should be appreciated that maternal electrocardiogram ECG and heart rate may be measured by standard skin ECG leads but the uterine electromyogram signal 91 may not.

Once signal 91 is received by antenna 26, signal 91 is then transmitted to monitor 28 via electrical leads 74. This electromyogram signal 91 provides an accurate indication of the beginning and end of a contraction. This information is essential for accurately determining the onset of parturition.

The generally accepted way to determine the progress of parturition is to time the interval between contractions. This method, while indicative of the general onset of parturition, is highly inaccurate for determining the exact progress of parturition and may be totally inaccurate due to false labor pains. Since the onset of labor pains are brought on by contractions, the measurement of contraction intervals is only one information source. The intensity of the contractions is another vital source of information in the determination of parturition. In the past, this intensity information was provided as a qualitative measurement by the mother to the health care professional. Thus the prior art does not disclose a quantitative method for measuring the intensity of uterine contractions as described above nor does it disclose an accurate method of determining the beginning or end of a contraction.

While this electromyogram information is indicative of parturition, false alarms may be generated. Therefore intra-uterine pressure is also utilized in the determination of parturition.

In a preferred embodiment of the invention, intra-uterine pressure is measured by a pressure transducer as described above. This information is then transmitted to monitor 28 in a fashion similar to that of the electromyogram signal 91. As may be seen in FIGS. 8 and 10A though 10D, curves of intra-uterine pressure 94 are illustrated. There are several characteristics which may be determined from the intra-uterine pressure. The duration or period P of a contraction may be determined by the fluctuation in intra-uterine pressure over a time period T. The time between contractions, indicated as C, may also be measured. Finally, the intensity of contractions I may be determined. Based upon any one of these or preferably a combination of the above, the onset and progress of parturition may be determined. In a preferred embodiment, the integral of the intra-uterine pressure taken over ten minute intervals is utilized to generate a contractibility index, generally denoted 96 in FIG. 9. The contractibility index 96 allows for the graphical representation of the progress of parturition. A medical professional may determine whether the contractions are indicative of a false labor or are actually the onset of parturition. As may be seen in FIG. 9, the contractility index may be broken up into four discrete regions, severe labor, moderate labor, mild labor and no labor. A medical professional may determine how far along the patient is by the magnitude of the last contractibility index reading. This is vitally important for determining if and when to perform a caesarean section, or for the administration of medication. In a preferred embodiment, a ten minute time period is utilized for determining the index values but it should be appreciated that any time interval may be utilized.

Additionally, fluctuations in intra-uterine pressure may be used to provide corrections to both the fetal electrocardiogram and maternal uterine electromyogram signals. The maternal electrocardiogram signal is illustrated in FIG. 6A as curve 93. These electromyogram and electrocardiogram signals are utilized to determine the health of both fetus 10 and mother 14 and the onset of parturition.

As may be seen form FIGS. 10A through 10D, there is a close correlation between increasing intra-uterine pressure and increases in electromyogram. This collaborates the theory that the myometrium contractions are causing the increase in intra-uterine pressure as opposed to application of an external force such as a situp, a hand pushing on the abdomen or possibly even gastric digestion. Thus, by correlating the intra-uterine pressure information with that of the electromyogram, false indications of labor are reduced.

Turning now to the use of the temperature information, maternal or fetal temperature also may be measured in a similar fashion to that described for the electromyogram signal 91 and electrocardiogram signal 90. As indicated above, there is a correlation between a drop in temperature of fetus 10 and mother 14 and the onset of parturition. While the prior art has suggested this correlation, it has failed to provide an accurate way of determining uterine or fetal temperature. But temperature alone is not a good indicator of the onset of parturition. The combination of temperature, intra-uterine pressure and electromyogram data provide the most accurate indication of the onset of parturition. This is because there must be a temperature drop in conjunction with elevated intra-uterine pressure and electromyogram response. It should be appreciated that the prior art neither teaches or suggests the monitoring of these three characteristics for determining parturition. Additionally, the invention contemplates the concept of monitoring maternal hear rate variability for monitoring maternal health.

Figure 10A:
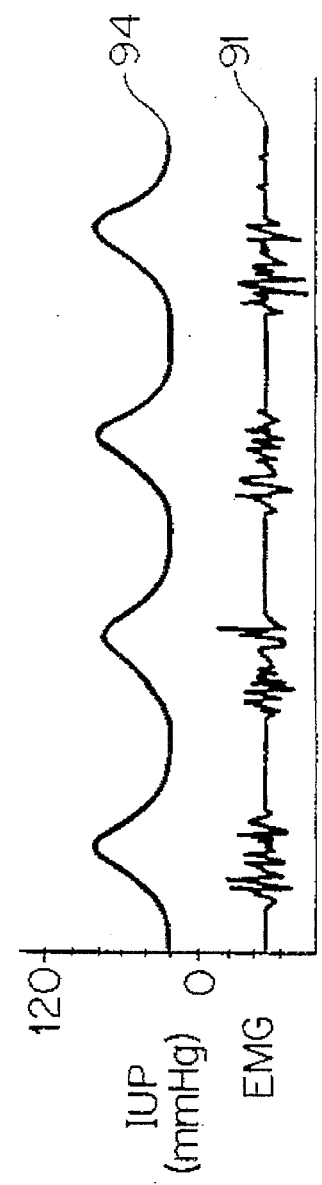
FIGS. 10A, 10B, 10C and 10D are plots of maternal intra-uterine pressure and electromyogram versus time for severe, moderate, mild and no labor, respectively.
Figure 10B:
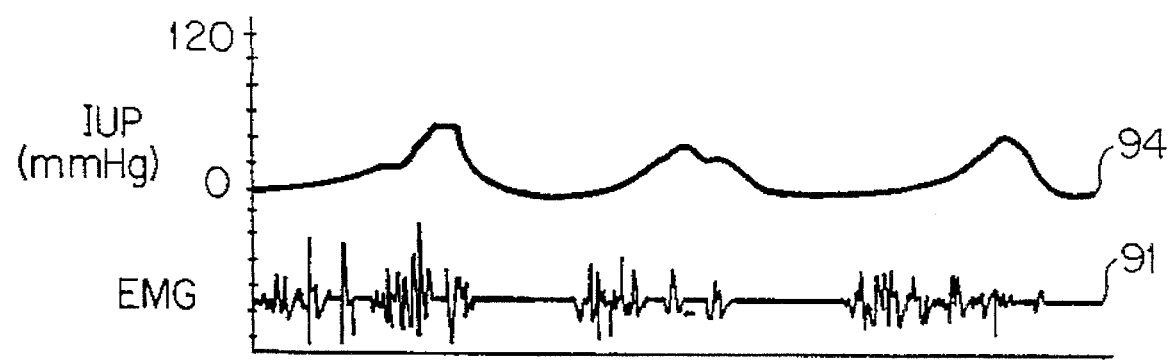
Figure 10C:
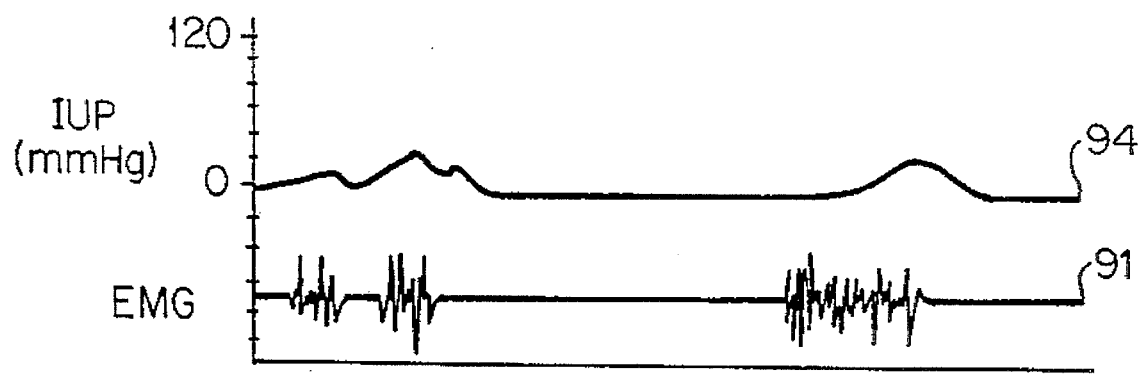
Figure 10D:
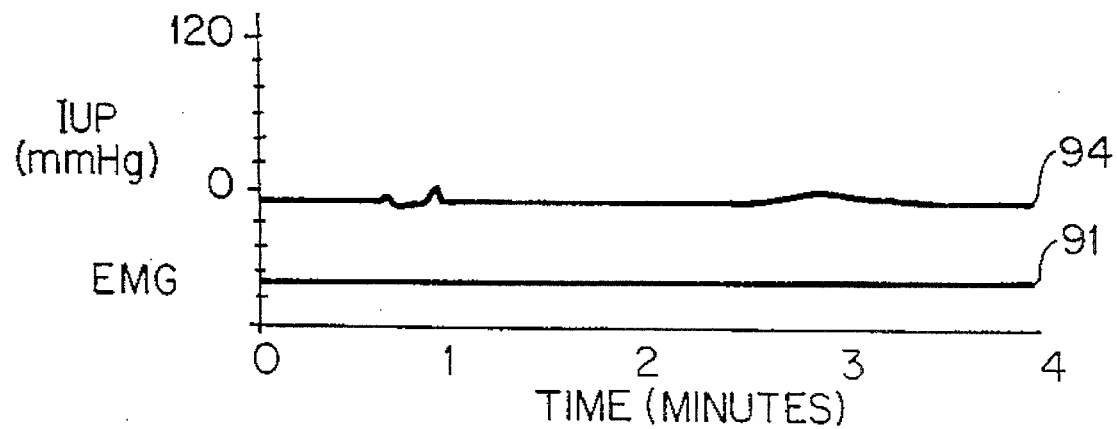

These signals in combination with the temperature, pressure and electromyogram signals may be utilized to automatically administer drugs from medication dispenser 24 for aiding or slowing the parturition process as described above. FIG. 10A through 10D illustrate the progressive effect of injecting a mother with labor inhibiting drugs of increasing dosages. As may be seen in FIG. 10A the patient is in severe labor with impending delivery. By injecting the patent with a labor inhibiting drug, the doctor may slow the labor process to a moderate level or mild level as illustrated in FIGS. 10B and 10C, respectively. The Doctor may even stop the labor process as indicated in FIG. 10D. The combination of intra-uterine pressure and electromyogram data provide an accurate indication of the onset of parturition. It should be appreciated that the prior art neither teaches or suggests the monitoring of both intra-uterine pressure and electromyogram data for the determination of parturition.

Finally, it should be appreciated that the prior art neither teaches or suggests the monitoring of fetus 10 for the determination of parturition. All prior art device focus on the mother and thus ignores the second most important participant in the birthing process.

Alternative Monitoring

This system may allow monitoring of fetus 10 while mother 14 is away from the hospital. This is accomplished by interfacing a standard ECG monitor 28 to a modem 98 at the medical facility and having a corresponding remote unit at the mother's remote location. The remote unit comprises a second modem 82 corresponding to the medical facility modem 98; a transceiver 100 for transmitting and receiving information to modem 82, an antenna 26" for receiving information from fetal monitor 20. In a preferred embodiment, transceiver 100 and antenna 26" are maintained in a wand shaped housing 102. Optional signal processing circuitry for providing compatibility between the remote sensing unit output signals and the ECG input signals may be provided. By using the radio-telemetry device described above and a conventional ECG 28, the signal processing circuitry may be eliminated.

In operation, the radio-telemetry signal 84 is received by antenna 26" as described above. Then this signal is processed by conventional signal processing circuitry to generate a signal compatible with modem 82. Modems 82 and 98 are conventional in nature and allow communication across a network 104. It should be appreciated that network 104 may be a packet switched network, a conventional telephone line, a T1 network or any other communications network functioning with or without encryption. Once the signal is received by modem 98, it is converted to a format compatible with monitor 28 which functions substantially as described above.

Medical Trials

Five trials have been performed during congenital diaphragmatic hernia repairs on human fetuses 10. The fetal electrocardiogram and temperature were recorded accurately, and demonstrated that the system 20 functioned in the electrically noisy operating room environment. Of note from these tests was the failure of other intra-operative fetal monitoring techniques. The skin electrodes failed to detect fetal electrocardiograms and the fetal pulse oximeter failed altogether in one case.

Postoperatively, adequate close monitoring of fetal electrocardiogram and temperature was maintained with the radio-telemetry monitoring device 20, described above, for over four weeks. Finally there were no complications associated with the radio-telemetry monitoring device 20.

Although the present invention has been fully described in connection with the preferred embodiment thereof with reference to the accompanying drawings, it is to be noted that various changes and modifications are apparent to those skilled in the art. Such changes and modifications are to be understood as included within the scope of the present invention as defined by the appended claims, unless they depart therefrom.

What is claimed is:

1. A method for implanting a fetal electrocardiogram monitoring device, said method comprising the steps of:

attaching a thin conductive electrode to a distal end of an electrocardiogram lead;

affixing the other end of said thin conductive electrode to a needle;

making an incision in the posterior abdominal wall of a fetus, said incision being wide enough to allow said needle, thin conductive electrode and lead to enter said fetus;

positioning said needle so as to thread said lead under the skin to the anterior abdominal wall of said fetus;

making a second incision for allowing said needle to be removed from said fetus, said second incision being wide enough to allow said needle and said thin conductive electrode to exit said fetus and narrow enough to prevent said lead from exiting said fetus.

2. The method recited in claim 1, further comprising the step of:

sealing said second incision by suturing said incision with said thin conductive electrode and thus maintaining said lead subcutaneously and preventing said lead from coming into contact with amniotic fluid.

* * * * *